(12) United States Patent
Poirier et al.

(10) Patent No.: US 9,110,000 B2
(45) Date of Patent: Aug. 18, 2015

(54) METHOD AND SYSTEM FOR DETERMINING THE POSITION OF AN ULTRASONIC WEDGE AND A PROBE

(75) Inventors: Jerome Poirier, Forges les Bains (FR); Anandamurugan S, Bangalore (IN)

(73) Assignee: General Electric Company, Schnectady, NY (US)

( * ) Notice: Subject to any disclaimer, the term of this patent is extended or adjusted under 35 U.S.C. 154(b) by 763 days.

(21) Appl. No.: 13/399,397

(22) Filed: Feb. 17, 2012

(65) Prior Publication Data

US 2013/0218490 A1 Aug. 22, 2013

(51) Int. Cl.
| | | |
|---|---|---|
| G01F 17/00 | (2006.01) |
| G01N 29/06 | (2006.01) |
| G01N 29/24 | (2006.01) |
| G01N 29/26 | (2006.01) |
| G01N 29/265 | (2006.01) |
| G01N 11/00 | (2006.01) |

(52) U.S. Cl.
CPC .......... *G01N 29/069* (2013.01); *G01N 29/2487* (2013.01); *G01N 29/262* (2013.01); *G01N 29/265* (2013.01); *G01N 2291/2675* (2013.01)

(58) Field of Classification Search
CPC ..................... G01N 29/265; G01N 2291/2675
See application file for complete search history.

(56) References Cited

U.S. PATENT DOCUMENTS

| | | | | |
|---|---|---|---|---|
| 6,789,427 B2 * | 9/2004 | Batzinger et al. | ............... | 73/614 |
| 6,938,457 B2 | 9/2005 | Johnson et al. | | |
| 2007/0068253 A1 * | 3/2007 | Carodiskey | ..................... | 73/570 |
| 2011/0239768 A1 | 10/2011 | Berke et al. | | |
| 2011/0247417 A1 | 10/2011 | Oberdoerfer et al. | | |

OTHER PUBLICATIONS

Noel Dube, et al., Mechanized Inspection of Girth Welds Using Ultrasonic Phase Arrays, Materials Research Institute, Waterloo, Canada, published in the 15th World Conference on Nondestructive Testing, Roma (Italy) Oct. 15-21, 2000.†

D. Shahriari, et al., "Development of an Expert Engineering Module for Determination of Ultrasonic Probe Position on the Weld Joint of Plate," Advanced Materials Research, vols. 83-86 (2010), pp. 1306-1314.†

Olympus NDT, Inc., Product PipeWIZARD, Phased Array System Version 2 User's Manual, Software Version 2.3, Manual Version 2.0, DUMG038C—Feb. 2002, Sold from 2000-2008 (approximately), http://www.olympus-ims.com/en/pipewizard/.†

\* cited by examiner
† cited by third party

*Primary Examiner* — Phuong Huynh
(74) *Attorney, Agent, or Firm* — Barclay Damon LLP

(57) ABSTRACT

A method and system for determining the position of an ultrasonic wedge and a probe is disclosed. The positioning method includes the steps of automatically determining the position of the ultrasonic wedge and the probe based on a number of parameters, including parameters that are based on the particular ultrasonic wedge and the probe as well as parameters based on the dimensions of the conduit and the girth weld.

5 Claims, 6 Drawing Sheets

METHOD AND SYSTEM FOR DETERMINING THE POSITION OF AN ULTRASONIC WEDGE AND A PROBE

BACKGROUND OF THE INVENTION

The subject matter disclosed herein relates to ultrasonic testing, and more particularly, a method and system for determining the position of an ultrasonic wedge and a probe.

Nondestructive testing devices can be used to inspect test objects to identify and analyze anomalies in the objects. Nondestructive testing allows an inspection technician to maneuver a probe at or near the surface of the test object in order to perform testing of both the object surface and underlying structure. Nondestructive testing can be particularly useful in some industries, e.g., aerospace, power generation, and oil and gas transport or refining, where inspection of test objects must take place without removal of the object from surrounding structures, and where hidden anomalies can be located that would otherwise not be identifiable through visual inspection. One example of nondestructive testing is ultrasonic testing. When conducting ultrasonic testing, an ultrasonic pulse can be emitted from an ultrasonic transducer of a probe and passed through a test object. Electric pulses can be generated by a transmitter and can be fed to the probe where they can be transformed into ultrasonic pulses by ultrasonic transducers. In some applications, the probe can be mounted on an ultrasonic wedge that provides intermediary physical contact between the ultrasonic transducer and the test object.

One type of ultrasonic transducer—a phased array transducer—comprises a plurality of electrically and acoustically independent transducer elements that incorporate piezoelectric ceramics. During operation, electrical waveform pulses are applied to the electrodes of the phased array transducer elements of the probe causing a mechanical change in the condition of the piezoelectric ceramics and generating ultrasonic signals (e.g. ultrasonic beams) that can be transmitted through the material to which the probe is coupled. By varying the timing of the electrical waveform pulses applied to the phased array transducer elements, the phased array transducer can generate ultrasonic beams at different angles, allowing the phased array transducer to steer the ultrasonic beam at different angles through the test object to try to detect anomalies. When an ultrasonic beam reflected from the material under inspection contacts the surface of the piezoelectric ceramic of a phased array transducer element, it generates a voltage difference across the electrodes that is detected as a receive signal by signal processing electronics. As the ultrasonic beams pass through the object, various pulse reflections called echoes occur as the ultrasonic beams interact with internal structures (e.g., anomalies) within the test object. By tracking the time difference between the transmission of the electrical pulse and the receipt of the electrical signal, and measuring the amplitude of the received ultrasonic signal, various characteristics of the material can be determined. These echoes allow the depth and size of anomalies within a given test object to be determined.

Another type of transducer—a time of flight diffraction (TOFD) transducer—comprises a transducer element that generates an ultrasonic beam that can be transmitted through the material to which the transmitter probe is coupled and received by another TOFD transducer in the receiver probe. The receiver probe will receive a lateral wave that travels along the surface between the transmitter probe and the receiver probe, and a back wall echo from the reflection of the ultrasonic beam off of the back wall. If the ultrasonic beam encounters any anomalies (e.g., a crack), the receiver probe will also receive a diffracted wave from the upper tip of the crack and a diffracted wave from the lower tip of the crack. These diffracted waves allow the depth and size of the anomaly to be determined.

In order to conduct the ultrasonic inspection of the test object, it is necessary to "set up" the inspection, including the precise position of the ultrasonic wedge and probe. For example, in order to conduct an ultrasonic inspection of a girth weld between two conduits using a phased array transducer, a technician must determine the position of the ultrasonic wedge and probe so that the ultrasonic scan sufficiently covers the weld and the areas of the conduits affected by the heat of the weld (i.e., the heat-affected areas) as well as determining the number of ultrasonic scans required. Similarly, in order to conduct an ultrasonic inspection of a girth weld between two conduits using a pair of TOFD transducers, a technician must determine the position of the ultrasonic wedges and probes so that the ultrasonic scan sufficiently covers the weld and the heat-affected areas of the conduits as well as determining the number of ultrasonic scans required. Once the position of the ultrasonic wedge and the probe is set, the inspection technician can rotate the devices around the conduits to circumferentially scan the girth weld.

A highly skilled and experienced ultrasonic technician employing complex mathematics is typically required to determine the proper position of the ultrasonic wedge and the probe as well as the number of ultrasonic scans. The ultrasonic technician must also locate the ultrasonic wedge and the probe in a manner that complies with industry standards and guidelines for conducting these inspections.

The discussion above is merely provided for general background information and is not intended to be used as an aid in determining the scope of the claimed subject matter.

BRIEF DESCRIPTION OF THE INVENTION

A method and system for determining the position of an ultrasonic wedge and a probe is disclosed. The positioning method includes the steps of automatically determining the position of the ultrasonic wedge and the probe based on a number of parameters, including parameters that are based on the particular ultrasonic wedge and the probe as well as parameters based on the dimensions of the conduit and the girth weld. An advantage that may be realized in the practice of some disclosed embodiments of the positioning method is to simplify the procedure of determining the correct position and the number of ultrasonic scans required.

In one embodiment, a system for conducting an ultrasonic scan of a girth weld between a first conduit and a second conduit is disclosed. The system comprises an ultrasonic wedge mounted on a first conduit, a probe mounted to a probe interface wall of the ultrasonic wedge, an ultrasonic inspection station connected to the probe by a probe cable, wherein the ultrasonic inspection station comprises a display, and a computer for creating an inspection plan, wherein the computer comprises a display, a microprocessor, a memory coupled to the microprocessor, and one or more executable instructions stored in the memory and configured to be executed by the processor for creating the inspection plan, the executable instructions including instructions for: determining an inspection procedure to be used for the ultrasonic scan, determining a first plurality of parameters for the ultrasonic wedge and the probe, determining a second plurality of parameters for the girth weld and at least one of the first conduit or the second conduit, and determining a position of the ultrasonic wedge and the probe on at least one of the first conduit or the second conduit for the ultrasonic scan based on the inspection procedure to be used, the first plurality of parameters, and the second plurality of parameters.

In another embodiment a method for automatically determining the position of an ultrasonic wedge and a probe for conducting an ultrasonic scan of a girth weld between a first conduit and a second conduit is disclosed. The method comprises the steps of determining an inspection procedure to be used for the ultrasonic scan, determining a first plurality of parameters for the ultrasonic wedge and the probe, determining a second plurality of parameters for the girth weld and at least one of the first conduit or the second conduit, and determining a position of the ultrasonic wedge and the probe on at least one of the first conduit or the second conduit for the ultrasonic scan based on the inspection procedure to be used, the first plurality of parameters, and the second plurality of parameters.

In yet another embodiment, a method for automatically determining the number of ultrasonic scans required for coverage of a girth weld between a first conduit and a second conduit by an ultrasonic wedge and a probe is disclosed. The method comprises the steps of determining the position of the ultrasonic wedge and the probe on at least one of the first conduit or the second conduit, and determining whether the ultrasonic scan conducted at the position of the ultrasonic wedge and the probe on at least one of the first conduit or the second conduit will cover the weld cap and the weld root of the girth weld.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1:
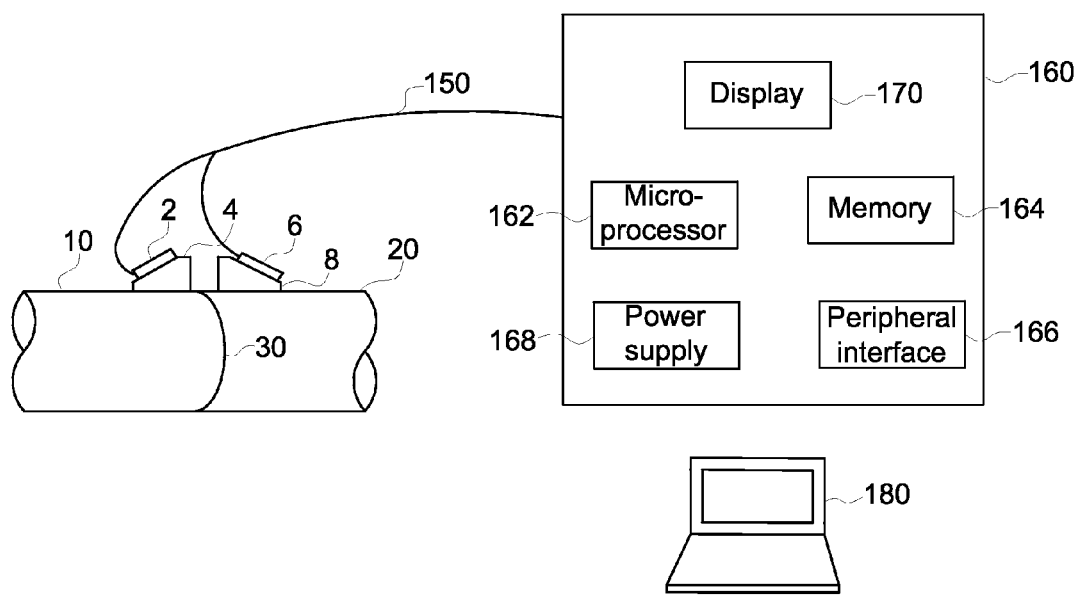
FIG. 1 is a block diagram of an exemplary ultrasonic testing system.

FIG. 1 is a block diagram of an exemplary ultrasonic testing system 10. In one embodiment, the ultrasonic testing system 100 is used to inspect a test object (e.g., a girth weld 30 joining two conduits 20, 22). The ultrasonic testing system 100 can comprise a first probe 2 (e.g., a phased array transducer probe or a TOFD probe) mounted on a first ultrasonic wedge 4 that can be attached to the first conduit 10. The first ultrasonic wedge 4 can be made from any material that has an acoustic velocity different from that of the test object. For example, some ultrasonic wedges are made from plastics such as plexi-glass or a polystyrene material through which sound travels at a known velocity. In one embodiment (e.g., when TOFD is used), the ultrasonic testing system 100 can comprise a second probe 6 (e.g., a TOFD probe) mounted on a second ultrasonic wedge 8 that can be attached to the second conduit 20.

One or more probe cables 150 can connect the probes 2, 6 to an ultrasonic inspection station 160, which can include one or more microprocessor(s) 162 for running system software and controlling system operations, and memory 164 coupled to the microprocessor 162. Computer program instructions (executable instructions) can be stored in memory 164 or available to be executed by the microprocessor 162 (e.g., downloadable from a network) can make up all or a portion of the software and software packages discussed herein. The ultrasonic inspection station 160 can also comprise a display 170 for viewing system operations and inspection results. Electronics in the ultrasonic inspection station 160 can transmit and receive ultrasonic signals. The received signals are typically processed through some type of analog to digital conversion, after which they are displayed as A-scans with amplitude on the y axis and time of flight on the x axis. These digital signals form the signature of a potential anomaly and are typically stored in memory 164 and post processed to provide additional views for the operator to assist in determining if an anomaly is truly a defect or not. The microprocessor 162 can provide control over the entire process. The ultrasonic inspection station 160 can also include a power supply 168, connected to an external power supply (e.g., AC voltage between 90V and 240V) or provided by rechargeable batteries.

The ultrasonic inspection station 160 can also include peripheral interfaces 166 for managing data being sent between the ultrasonic inspection station 160 and other components. For example, in one embodiment, the peripheral interfaces 166 can include a USB, Ethernet (LAN), or wireless interface (WLAN) for receiving and loading an inspection plan prepared on a computer 180 or other device remote from the test object and validated by an inspection plan creator using inspection plan creation software. As will be described, the inspection plan creator can use the inspection plan creation software on the computer 180 or other device to automatically determine the proper position of the ultrasonic wedges and the probes as well as the number of ultrasonic scans. The computer 180 or other device can include a display, microprocessor, a memory coupled to the microprocessor, and one or more executable instructions stored in the memory and configured to be executed by the processor for creating the inspection plan.

Figure 2:
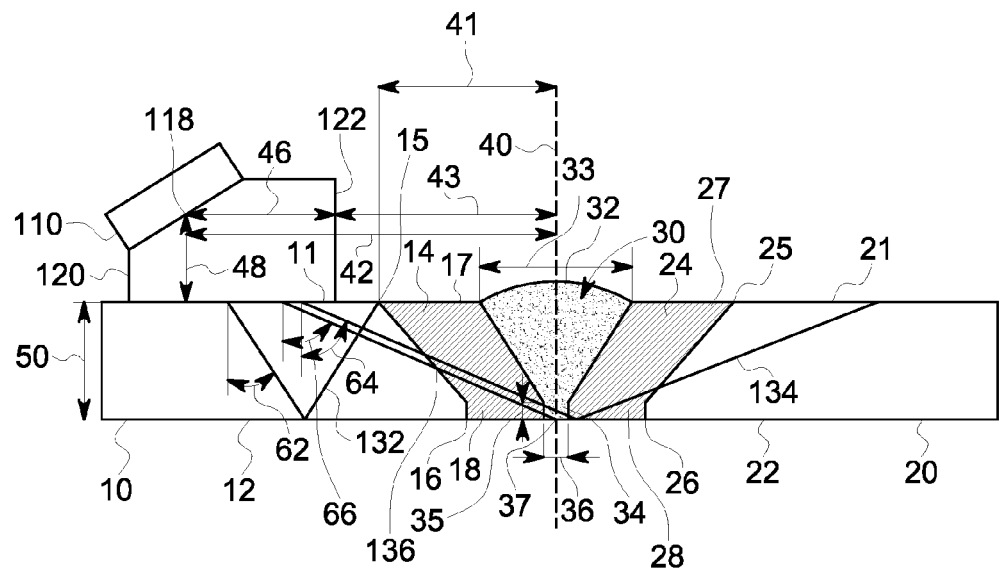
FIG. 2 illustrates an exemplary phased array transducer probe and an ultrasonic wedge positioned to conduct an ultrasonic scan of the weld cap of an exemplary girth weld between two conduits.

FIG. 2 illustrates an exemplary phased array transducer probe 110 and an ultrasonic wedge 120 positioned to conduct an ultrasonic scan of the weld cap 32 of an exemplary girth weld 30 between two conduits 10, 20. The first conduit 10 and the second conduit 20 each have a thickness (T) 50. The exemplary girth weld 30 is a V type weld with weld cap 32 (or overcap) having a weld cap width ($W_C$) 33 and a weld root 34 having a root height (H) 35 and width ($W_R$) 36. It will be understood that the described invention can be used with other type of welds (e.g., J-welds, VV-welds, etc.).

As shown in FIG. 2, the girth weld 30 has a centerline 40. The girth weld 30 can be made of a molten metal matching the material of the conduits 10, 20 (e.g., carbon steel). When the girth weld 30 is formed at high temperatures, the first heat-affected area 14 (having a top edge 15 and a bottom edge 16) of the first conduit 10 and the second heat-affected area 24 (having a top edge 25 and a bottom edge 26) of the second conduit 20 will also experience high temperatures. In order to inspect the girth weld 30 and the heat-affected areas 14, 24 of the conduits 10, 20 for any anomalies, a phased array transducer probe 10 and ultrasonic wedge 120 can be installed on the conduits 10, 20 to conduct ultrasonic scans.

As shown in FIG. 2, in one embodiment of the invention, in order to conduct an ultrasonic scan of the weld cap 32, the top portion 17 of the first heat-affected area 14, and the top portion 27 of the second heat-affected area 24, the position of the ultrasonic wedge 120 and phased array transducer probe 110 on the outer wall 11 of the first conduit 10 is determined so that the first (or start) refracted beam 132 provides ultrasonic scan coverage starting proximate to the top edge 15 of the first heat-affected area 14 on the outer wall 11 proximate to the weld cap 32. For example, the position of the ultrasonic wedge 120 and phased array transducer probe 110 can be determined so that the first refracted beam 132 enters the first conduit 10 at a first (or start) refracted beam angle 62 (e.g., Angle Start=35 degrees) and then reflects off of the back wall 12 of the first conduit 10 to a point proximate to the top edge 15 of the first heat-affected area 14 on the outer wall 11 located at a horizontal distance (A) 41 from the weld centerline 40. This position of the ultrasonic wedge 120 and phased array transducer probe 110 on the outer wall 11 of the first conduit 10 can result in the last (stop) refracted beam 134 entering the first conduit at a last (stop) refracted beam angle 64 (e.g., Angle Stop=70 degrees) and then reflecting off of the back wall 22 of the second conduit 20 to a point past the top edge 25 of the second heat-affected area 24 on the front wall 21.

It will be understood that the ultrasonic wedge 120 and phased array transducer probe 110 can generate a plurality of ultrasonic beams between the first refracted beam 132 and the last refracted beam 134 (e.g., ultrasonic beams spaced every 1 degree) to provide a full ultrasonic scan of the weld cap 32, the top portion 17 of the first heat-affected area 14, and the top portion 27 of the second heat-affected area 24. The ultrasonic scan of the girth weld 30 at this position can be conducted by rotating the ultrasonic wedge 120 and probe 110 around the first conduit 10 to circumferentially scan the girth weld 30. To complete the inspection of the weld cap 32, the top portion 17 of the first heat-affected area 14, and the top portion 27 of the second heat-affected area 24, if access is available, the ultrasonic wedge 120 and phased array transducer probe 110 can then be positioned at the mirror-image position on the outer wall 21 of the second conduit 20 on the other side of the weld centerline 40. While the ultrasonic scan conducted with the ultrasonic wedge 120 and probe 110 positioned as shown in FIG. 2 does provide complete coverage of the weld cap 32, the top portion 17 of the first heat-affected area 14, and the top portion 27 of the second heat-affected area 24, the ultrasonic scan does not necessarily provide complete coverage of the weld root 34 or the bottom portion 28 of the second heat-affected area 24.

Figure 3:
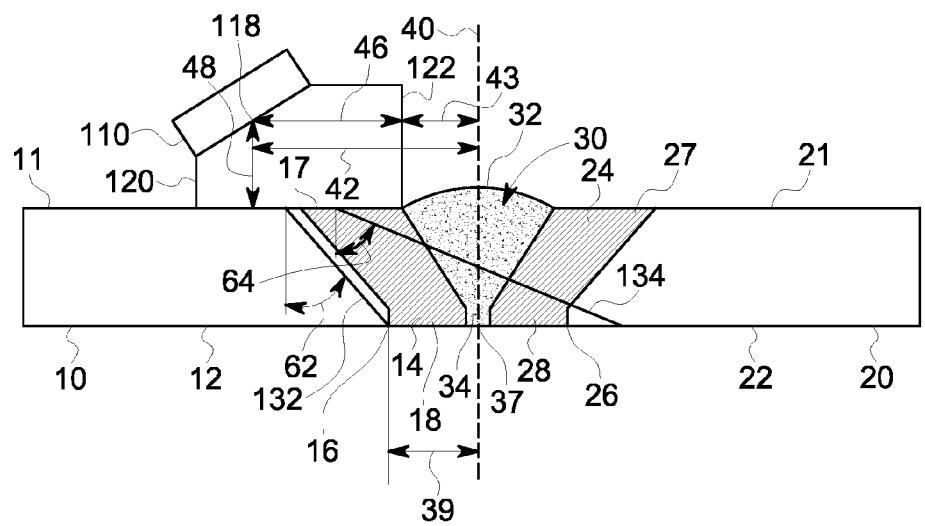
FIG. 3 illustrates an exemplary phased array transducer probe and an ultrasonic wedge positioned to conduct an ultrasonic scan of the weld root of an exemplary girth weld between two conduits.

FIG. 3 illustrates an exemplary phased array transducer probe 110 and an ultrasonic wedge 120 positioned to conduct an ultrasonic scan of the weld root 34. As shown in FIG. 3, in one embodiment of the invention, in order to conduct an ultrasonic scan of the weld root 34, the bottom portion 18 of the first heat-affected area 14, and the bottom portion 28 of the second heat-affected area 24, the position of the ultrasonic wedge 120 and phased array transducer probe 110 on the outer wall 11 of the first conduit 10 is determined so that the first (or start) refracted beam 132 provides ultrasonic scan coverage starting proximate to the bottom edge 16 of the first heat-affected area 14 on the back wall 12 proximate to the weld root 34. For example, the position of the ultrasonic wedge 120 and phased array transducer probe 110 can be determined so that the first refracted beam 132 enters the first conduit 10 at a first refracted beam angle 62 (e.g., Angle Start=35 degrees) and travels to the back wall 12 to a point proximate to the bottom edge 16 of the first heat-affected area 14 on the back wall 12 located at a horizontal distance (B) 39 from the weld centerline 40. As shown in FIG. 3, this position of the ultrasonic wedge 120 and phased array transducer probe 110 on the outer wall 11 of the first conduit 10 can result in the last (stop) refracted beam 134 entering the first conduit at a last (stop) refracted beam angle 64 (e.g., 70 degrees) and then travels to the back wall 22 of the second conduit 20 at a point past the bottom edge 26 of the second heat-affected area 24 on the back wall 22, providing complete coverage of the weld root 34, the bottom portion 18 of the first heat-affected area 14, and the bottom portion 28 of the second heat-affected area 24. The ultrasonic scan at this position can be conducted by rotating the ultrasonic wedge 120 and probe 110 around the first conduit 20 to circumferentially scan the girth weld 30. To complete the inspection of the weld root 34, the bottom portion 18 of the first heat-affected area 14, and the bottom portion 28 of the second heat-affected area 24, if access is available, the ultrasonic wedge 120 and phased array transducer probe 110 can then be positioned at the mirror-image position on the outer wall 21 of the second conduit 20 on the other side of the weld centerline 40.

Referring again to FIGS. 2 and 3, the position of the ultrasonic wedge 120 and phased array transducer probe 110 that will produce the desired first refracted beam 132 and required ultrasonic scan coverage can be determined based on a number of parameters, including parameters that are based on the particular ultrasonic wedge 120 and phased array transducer probe 110 used (e.g., ultrasonic wedge X offset ($X_O$) 46 and the ultrasonic wedge Z offset ($Z_O$) 48) as well as parameters based on the dimensions of the first conduit (e.g., diameter (d), thickness (T) 50) and the girth weld 30 (e.g., the width ($W_C$) 33 of the weld cap 32, the height (H) 35 of the weld root 34). The horizontal distance (D) 43 from the weld centerline 40 to the ultrasonic wedge front face 122 (and the horizontal distance (E) 42 from the weld centerline 40 to probe center element ($C_0$) 118) set the position of the ultrasonic wedge 120 and phased array transducer probe 110 and can be determined based on these and other parameters.

Figure 4:
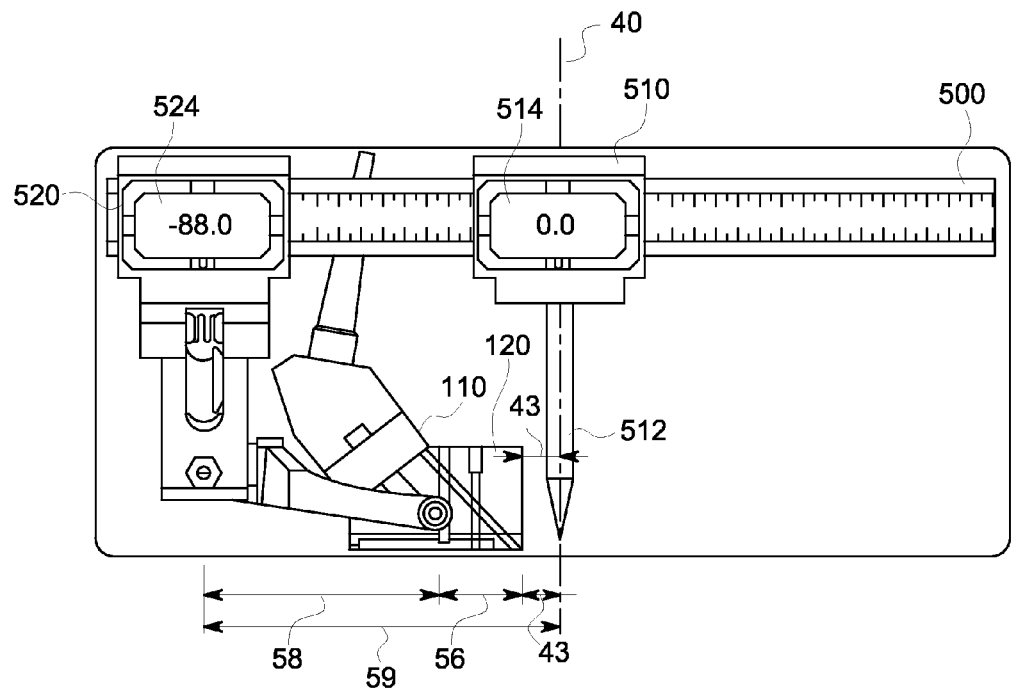
FIG. 4 illustrates an exemplary image of a scanner ruler for positioning a phased array transducer probe and an ultrasonic wedge to conduct an ultrasonic scan.

FIG. 4 illustrates an exemplary image of a scanner ruler 500 for positioning a phased array transducer probe 110 and an ultrasonic wedge 120 to conduct an ultrasonic scan. This image can be shown to an inspection technician on the display 170 of the ultrasonic inspection station 160 (FIG. 1) to provide instructions on positioning the phased array transducer probe 110 and an ultrasonic wedge 120. The information about the scanner ruler 500 and its related dimensions is part of the inspection plan prepared by the inspection plan creator, which provides the proper position of the devices for conducting the ultrasonic scan. The scanner ruler 500 depicted in the image represents a device attached to one of the conduits 10, 20 that facilitates positioning, attachment, and rotation of the phased array transducer probe 110 and the ultrasonic wedge 120 on the conduits circumferentially scan the girth weld 30. The scanner ruler 500 provides dimensions relative to a weld centerline 40 (e.g., 0.0 mm) to position the phased array transducer probe 110 and the ultrasonic wedge 120 at a precise horizontal distance away from the weld centerline 40.

As shown in FIG. 4, the inspection plan calls for the center scanner ruler attachment 510 to be positioned on the weld centerline 40 at the center scanner ruler attachment position 514 (e.g., 0.0 mm) on the scanner ruler 500. A weld centerline locator 512 extends from the center scanner ruler attachment 510 to facilitate placement of the center scanner ruler attachment 510 on the weld centerline 40. The inspection plan calls for the left scanner ruler attachment 520 to be positioned at a certain left scanner ruler attachment position 524 (e.g., −88.0 mm) at a certain horizontal distance (H) 59 from the weld centerline 40 given by the following equation:

$$H = D + F + G \qquad (1)$$

where
H=horizontal distance 59 from the weld centerline 40 to the position 524 of the left scanner ruler attachment 520;
D=horizontal distance 43 from the weld centerline 40 to the ultrasonic wedge front face 122;
F=horizontal distance 56 from the ultrasonic wedge front face 122 to the left scanner ruler attachment 520 to the ultrasonic wedge 120; and
G=horizontal distance 58 from the left scanner ruler attachment 520 to the ultrasonic wedge 120 to the scanner ruler 500.

Since the horizontal distances (F) 56 and (G) 58 are fixed by the physical dimensions of the scanner ruler 500 and the ultrasonic wedge 120, the inspection plan creation software can determine the required horizontal distance (D) 43 from the weld centerline 40 to the ultrasonic wedge front face 122 to provide the position of the ultrasonic wedge 120 and phased array transducer probe 110 that will produce the desired first refracted beam 132 and required ultrasonic scan coverage.

Figure 5:
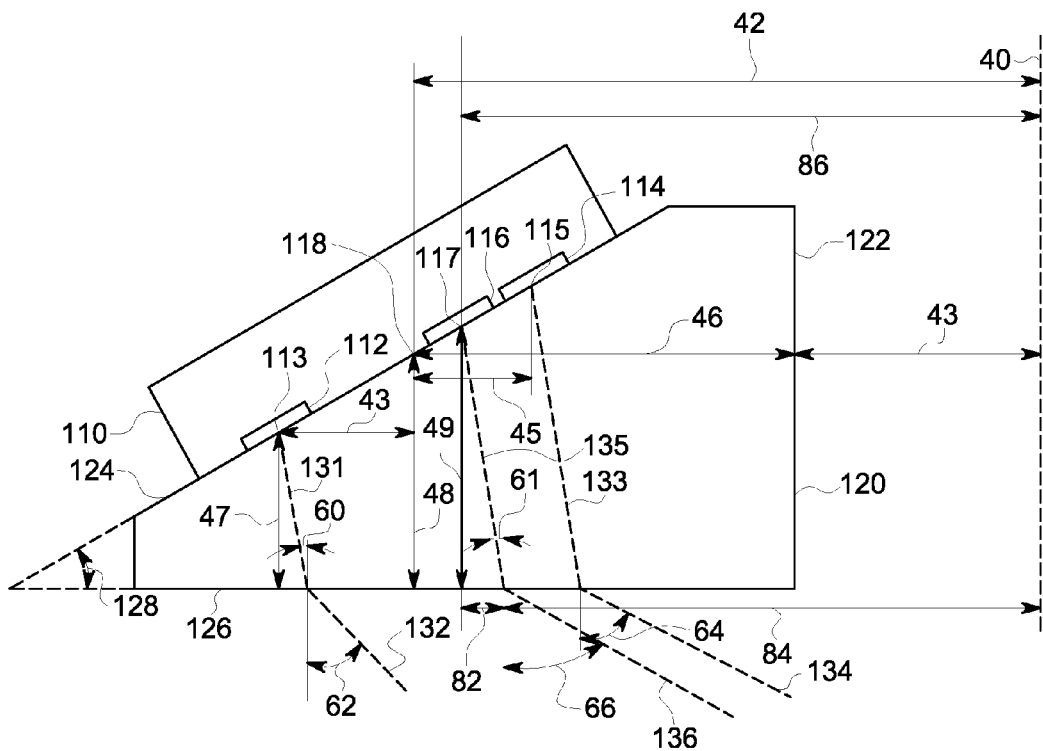
FIG. 5 illustrates parameters of an exemplary phased array transducer probe and an ultrasonic wedge.

FIG. 5 illustrates parameters of an exemplary phased array transducer probe 110 (having $N_0$ elements) and an ultrasonic wedge 120. Some or all of the following list of parameters shown in FIG. 5 (and in FIGS. 2 and 3) can be used or calculated to automatically determine the horizontal distance (D) 43 from the weld centerline 40 to the ultrasonic wedge front face 122 in an inspection plan: the width ($W_C$) 33 of the weld cap 32, the height (H) 35 and the width ($W_R$) 36 of the weld root 34, the horizontal distance (B) 39 from the weld centerline 40 to the bottom edge 16 of the first heat-affected area 14 (e.g., the width of the bottom portion 18 of the heat-affected area 14 plus one half of the width ($W_R$) 33 of the weld root 34), the horizontal distance (A) 41 from the weld centerline 40 to the top edge 15 of the first heat-affected area 14 (e.g., the width of the top portion 17 of the heat-affected area 14 plus one half of the width ($W_C$) 33 of the weld cap 32), the horizontal distance (E) 42 from the weld centerline 40 to the probe center element ($C_0$) 118, the horizontal distance (D) 43 from the weld centerline 40 to the ultrasonic wedge front face 122, the horizontal distance ($P_{X1}$) 44 between the probe center element ($C_0$) 118 and the first (start) center element ($C_1$) 113 of the first (start) aperture 112, the horizontal distance ($P_{Xn}$) 45 between the probe center element ($C_0$) 118 and the last (stop) aperture center element ($C_n$) 115 of the last (stop) aperture, the ultrasonic wedge X offset ($X_0$) 46 from the ultrasonic wedge probe interface wall 124 to the ultrasonic wedge front face 122, the first (start) Z offset ($Z_1$) 47 from the ultrasonic wedge probe interface wall 124 to the ultrasonic wedge back wall 128, the ultrasonic wedge Z offset ($Z_0$) 48 from the ultrasonic wedge probe interface wall 124 to the ultrasonic wedge back wall 128, the weld centerline beam Z offset ($Z_{WC}$) 49 from the ultrasonic wedge probe interface wall 124 to the ultrasonic wedge back wall 128, the conduit thickness (T) 50 and diameter (d), the first (start) refracted beam angle 62 (Angle Start), the last (stop) refracted beam angle 64 (Angle Stop), the weld centerline refracted beam angle (α) 66, the horizontal emission distance ($E_{WC}$) 82 from the emission point of the weld centerline beam aperture center element ($C_{WC}$) 117 of the weld centerline beam aperture 116 to the weld centerline refracted beam 136, the horizontal transmission distance ($T_{WC}$) 84 from the weld centerline refracted beam 136 to the weld centerline 40, the horizontal beam distance ($L_{WC}$) from the from the emission point of the weld centerline beam aperture center element ($C_{WC}$) 117 of the weld centerline beam aperture 116 to the weld centerline 40, the ultrasonic wedge angle 128, the first (start) center element emission beam 131, the first (start) refracted beam 132, the last (stop) aperture center element emission beam 133, the last (stop) refracted beam 134, the weld centerline beam aperture center element ($C_{WC}$) emission beam 135, the weld centerline refracted beam 136, the wedge velocity ($V_W$) (e.g., 2,380 m/s for steel) and longitudinal velocity ($V_L$) (e.g., 5,920 m/s for steel) of the ultrasonic wedge 120, and the shear velocity ($V_S$) (e.g., 3,230 m/s for steel) of the material of the conduits 10, 20.

Figure 6:
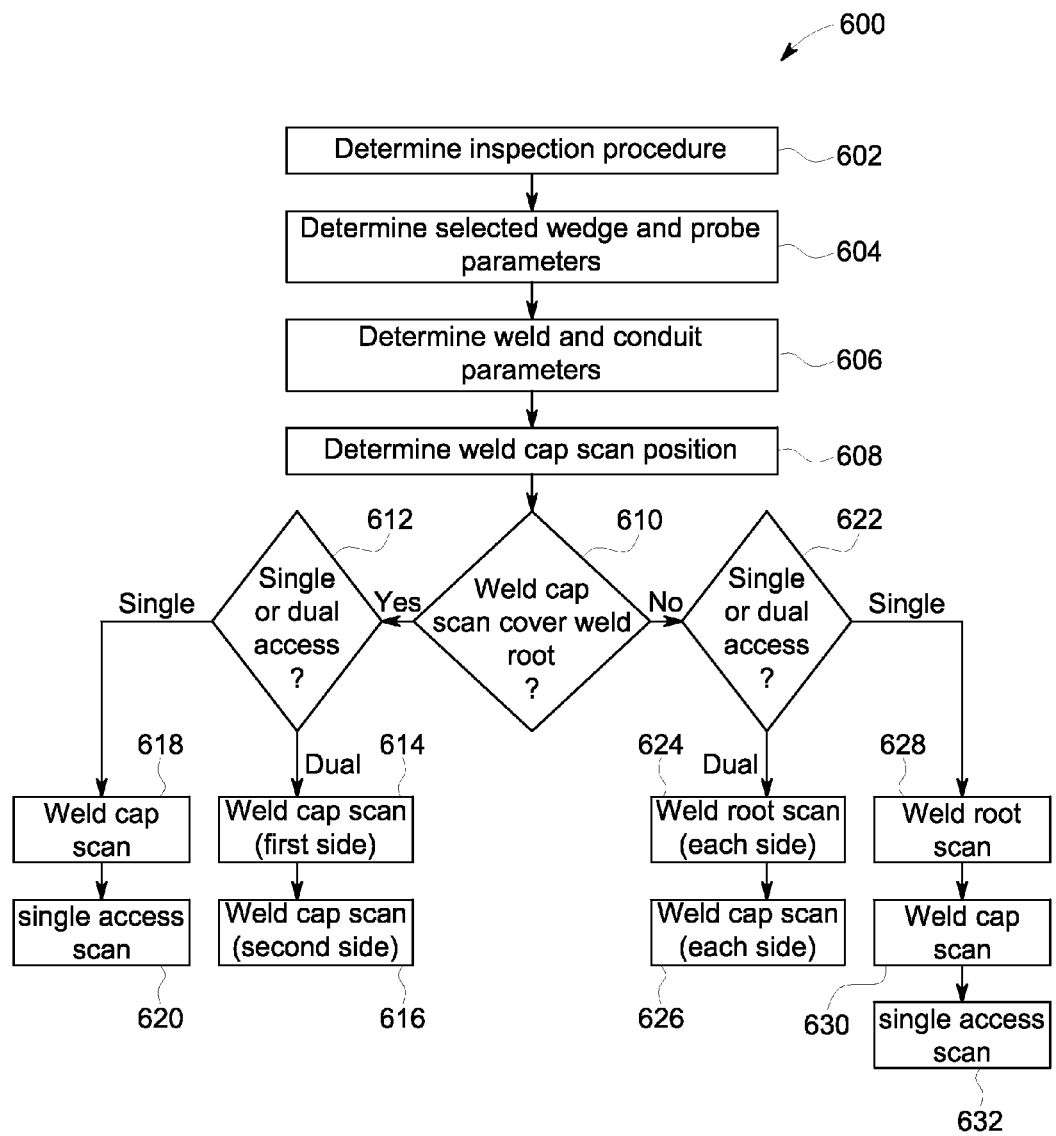
FIG. 6 is an exemplary method of determining the position of an ultrasonic wedge and phased array transducer probe.

FIG. 6 is an exemplary method 600 of determining the position of an ultrasonic wedge 120 and phased array transducer probe 110. The inspection plan creator can use the inspection plan creation software on the computer 180 (FIG. 1) or another device to automatically determine the proper position of the ultrasonic wedge 120 and the phased array transducer probe 110, as well as the number of ultrasonic scans. At step 602, the inspection plan creation software can determine the inspection procedure to be used for the ultrasonic scan based on the selection by the inspection plan creator of one or more inspection procedures programmed in the inspection plan creation software on the computer 180 for conducting the ultrasonic scan of the girth weld 30 and heat-affected areas 14, 24. The selected inspection procedures can include a number of technical requirements that must be satisfied in order to comply with standards or guidelines for conducting the inspection of the girth weld 30.

Based on the inspection procedure selected by the inspection plan creator, the inspection plan creation software can identify one or more ultrasonic wedges 120 and phased array transducer probes 110 for selection by the inspection plan creator for conducting the ultrasonic scan of the girth weld 30 and heat-affected areas 14, 24. At step 604, the inspection plan creation software can determine a plurality of the parameters discussed above for the selected combination of the ultrasonic wedge 120 and phased array transducer probe 110 that can be programmed into the inspection plan creation software.

In addition, at step 606, the inspection plan creation software can determine a plurality of the parameters discussed above for the girth weld 30 and conduits 10, 20. For example, the inspection plan creator can enter the width ($W_C$) 33 of the weld cap 32, the height (H) 35 of the weld root (34), the conduit thickness (T) 50 and diameter (d), and the conduit material on the computer 180. For example, the information concerning the conduit can be provided by the inspection plan creator by selecting a nominal conduit size, wherein the inspection plan creation software can then provide the parameters for that conduit.

Once the parameters for the ultrasonic wedge 120, phased array transducer probe 110, conduits 10, 20, and girth weld 30 are known, at step 608, the inspection plan creation software can automatically determine the position of the devices on the conduits 10, 20 for the ultrasonic scan of the weld cap 30. For example, the inspection plan creation software can use the following equations to determine the position of the ultrasonic wedge 120 and phased array transducer probe 110 (e.g., the horizontal distance (D) 43 from the weld centerline 40 to the ultrasonic wedge front face 122) to conduct an ultrasonic scan of the weld cap 32, the top portion 17 of the first heat-affected area 14, and the top portion 27 of the second heat-affected area 24 as shown in FIG. 2.

$$D = E - X_0 \quad (2)$$

$$\text{Start Incident Angle} = \arcsin[\sin(\text{Angle Start}) * (V_W/V_S)] \quad (3)$$

$$\text{If } Z < Z_0, E = [2*T*\tan(\text{Angle Start})] + [Z*\tan(\text{Start Incident Angle})] + P_X + A \quad (4)$$

$$\text{If } Z >= Z_0, E = [2*T*\tan(\text{Angle Start})] + [Z*\tan(\text{Start Incident Angle})] - P_X + A \quad (5)$$

Where
D=horizontal distance 43 from the weld centerline 40 to the ultrasonic wedge front face 122;
E=horizontal distance 42 from the weld centerline 40 to the probe center element ($C_0$) 118
$X_0$=X offset 46
Start Incident Angle=first (start) beam incident angle 60;
Angle Start=first (start) refracted beam angle 62;
$V_W$=Wedge Velocity;
$V_S$=Shear Velocity;
Z=the active (e.g., start) aperture Z offset ($Z_1$) 47;
$Z_0$=ultrasonic wedge Z offset 48;
$P_X$=the horizontal distance 44 between probe center element ($C_0$) 118 and the active (e.g., start) aperture center element ($C_1$) 113; and
A=horizontal distance 41 from the weld centerline 40 to the top edge 15 of the first heat-affected area 14.

In addition to determining the position of the ultrasonic wedge 120 and phased array transducer probe 110 for the ultrasonic scan of the weld cap 32, the inspection plan creation software can also determine the number of ultrasonic scans required for complete or maximum coverage of the girth weld 30 (e.g., complete coverage of the weld cap 32, weld root 34, and heat-affected areas 14, 15). At step 610, the inspection plan creation software can determine whether the position of the ultrasonic wedge 120 and the phased array transducer probe 110 determined at step 608 for conducting the ultrasonic scan of the weld cap 32 will also provide coverage of the weld root 34. In one embodiment, the inspection plan creation software can make that determination at step 610 by determining the weld centerline refracted beam angle ($\alpha$) 66 of the weld centerline refracted beam 136 that intersects with the weld centerline 40 at the weld root center 37 when the ultrasonic wedge 120 and phased array transducer probe 110 are positioned to conduct an ultrasonic scan of the weld cap 32 (FIGS. 2 and 5). In one embodiment, the inspection plan creation software can use an iterative process to determine the weld centerline refracted beam angle ($\alpha$) 66 using the following equations in the first iteration:

$$\alpha_1 = (\text{Angle Start} + \text{Angle Stop})/2 \quad (6)$$

$$I_{WC} = \arcsin[\sin(\alpha_1)*(V_W/V_S)] \quad (7)$$

$$B_1 = \alpha_1/2 \quad (8)$$

$$T_{WC} = T*\tan(\alpha_1) \quad (9)$$

$$E_{WC} = Z_0*\tan(I_{WC}) \quad (10)$$

$$L_{WC1} = T_{WC} + E_{WC} \quad (11)$$

$$X = D + X_0 \quad (12)$$

$$\text{If } L_{WC1} > X, (\alpha_1 = \alpha_1 - B_1), \text{ else } (\alpha_1 = \alpha_1 + B_1) \quad (13)$$

Where
$\alpha_1$=calculated first weld centerline refracted beam angle 66;
Angle Start=first (start) refracted beam angle 62;
Angle Stop=last (stop) refracted beam angle 64;
$I_{WC}$=weld centerline beam incident angle 61;
$V_W$=Wedge Velocity;
$V_S$=Shear Velocity;
B=Step Angle;
$T_{WC}$=horizontal transmission 84 distance from the weld centerline refracted beam 136 to the weld centerline 40;
T=conduit thickness 50;
$E_{WC}$=horizontal emission distance 82 from the weld centerline beam aperture center element ($C_{WC}$) 117 emission point to the weld centerline refracted beam 136;
$Z_0$=ultrasonic wedge Z offset 48;
$L_{WC}$=the horizontal beam distance 86 from the weld centerline beam aperture center element ($C_{WC}$) 117 emission point to the weld centerline 40;
D=horizontal distance 43 from the weld centerline 40 to the ultrasonic wedge front face 122; and
$X_0$=ultrasonic wedge X offset (46).

Subsequent iterations can continue for a predetermined number of minimum iterations or until the horizontal beam distance ($L_{WCn}$) 86 from the weld centerline beam aperture center element ($C_{WC}$) 117 emission point to the weld centerline 40 for one iteration is equal to the horizontal beam distance ($L_{WCn-1}$) 86 of the prior iteration. In one embodiment, the subsequent iterations use the following equations:

$$\alpha_n = \alpha_{n-1} \quad (14)$$

$$I_{WC} = \arcsin[\sin(\alpha_n)*(V_W/V_S)] \quad (15)$$

$$B_n = B_{n-1}/2 \quad (16)$$

$$T_{WC} = T*\tan(\alpha_n) \quad (17)$$

$$E_{WC} = Z_0*\tan(I_{WC}) \quad (18)$$

$$L_{WCn} = T_{WC} + E_{WC} \quad (19)$$

$$X = D + X_0 \quad (20)$$

If $L_{WCn} > X$, $(\alpha_n = \alpha_n - B_1)$, else $(\alpha_n = \alpha_n + B_1)$ (21)

If $L_{WCn} = L_{WCn-1}$, $\alpha = \alpha_n$, else continue iteration (22)

The weld centerline refracted beam angle ($\alpha$) 66 can then be compared to a weld centerline beam threshold angle (e.g., $\alpha_{TH} = 60$ degrees). For example, if the weld centerline refracted beam angle ($\alpha$) 66 is less than or equal to the weld centerline beam threshold angle ($\alpha_{TH}$), that would indicate that the ultrasonic wedge 120 and phased array transducer probe 110 were positioned close enough to the girth weld 30 that the ultrasonic scan for the weld cap 32 also covers the weld root 34. If the weld centerline refracted beam angle ($\alpha$) 66 is greater than the weld centerline beam threshold angle ($\alpha_{TH}$), that would indicate that the ultrasonic wedge 120 and phased array transducer probe 110 were positioned too far from the girth weld 30 that the ultrasonic scan for the weld cap 32 also does not also cover the weld root 34.

Returning to FIG. 6, at step 610, if the inspection plan creation software determines that the ultrasonic scan for the weld cap 32 does not also cover the weld root 34 (e.g., if $\alpha > \alpha_{TH}$), at step 622, the inspection plan creation software determines whether the ultrasonic wedge 120 and the phased array transducer probe 110 can be positioned on both sides (dual access) of the girth weld 30 or on only one side (single access). For example, the inspection plan creator can enter whether single access or dual access is available. If there is access to perform an ultrasonic scan on both the left (first) side (i.e., on the first conduit 10) and the right (second) side (i.e., on the second conduit 20) of the girth weld 30 (FIG. 2), the inspection plan creation software determines that two ultrasonic scans (or passes) on each side of the girth weld 30 (for scanning the weld root 34 on each side (in step 624) and for scanning the weld cap 32 on each side (in step 626)) are required for complete coverage of the girth weld 30, the first heat-affected area 14, and the second heat-affected area 24. If there is only access to perform an ultrasonic scan on one side of the girth weld 30, the inspection plan creation software determines that a total of three ultrasonic scans (or passes) may be needed on that side of the girth weld 30 (e.g., for scanning the weld root 34 on that side (in step 628), for scanning the weld cap 32 on that side (in step 630), and for a single access scan (in step 632)).

If an ultrasonic scan of the weld root 34 is required, the inspection plan creation software can use equation (2) above along with the following equations to determine the position (D) 43 of the ultrasonic wedge 120 and phased array transducer probe 110 of the girth weld 30 to conduct an ultrasonic scan of the weld root 34, the bottom portion 18 of the first heat-affected area 14, and the bottom portion 28 of the second heat-affected area 24 as shown in FIG. 3:

If $Z < Z_0$, $E = [T^* \tan(\text{Angle Start})] + [Z^* \tan(\text{Start Incident Angle})] + P_X + B$ (23)

If $Z >= Z_0$, $E = [T^* \tan(\text{Angle Start})] + [Z_1^* \tan(\text{Start Incident Angle})] - P_X + B$ (24)

Where
B = the horizontal distance 39 from the weld centerline 40 to the bottom edge 16 of the first heat-affected area 14; and
$Z_1$ = first (start) Z offset 47 from the ultrasonic wedge probe interface wall 124 to the ultrasonic wedge back wall 128.

As can be seen in FIG. 3, if the horizontal distance (D) 43 from the weld centerline 40 to the ultrasonic wedge front face 122 is less than one half of the weld cap width ($W_C$) 33, that would require that the ultrasonic wedge 120 be placed on top of the weld cap 32. Accordingly, if the inspection plan creation software calculates the horizontal distance (D) 43 from the weld centerline 40 to the ultrasonic wedge front face 122 to be less than one half of the weld cap width ($W_C$) 33, the distance (D) 43 is set to be equal to one half of the weld cap width ($W_C$) 33.

If $D < 0.5^* W_C$, $D = 0.5^* W_C$ (25)

In one embodiment of the invention, in order to conduct a single access ultrasonic scan (similar to the weld root 34 scan of FIG. 3), the position of the ultrasonic wedge 120 and phased array transducer probe 110 on the outer wall 11 of the first conduit 10 is determined so that the first (or start) refracted beam 132 provides ultrasonic scan coverage starting proximate to the center 37 of the weld root 33 (as shown in FIG. 3). For example, the position of the ultrasonic wedge 120 and phased array transducer probe 110 can be determined so that the first refracted beam 132 enters the first conduit 10 at a first refracted beam angle 62 (e.g., Angle Start=35 degrees) and travels to the back wall 12 proximate to the center 37 of the weld root 33 (as shown in FIG. 3). The ultrasonic scan at this position can be conducted by rotating the ultrasonic wedge 120 and probe 110 around the first conduit 20 to circumferentially scan the girth weld 30.

If a single access ultrasonic scan of is required, the inspection plan creation software can also use equation (2) above along with the following equations to determine the position (D) 43 of the ultrasonic wedge 120 and phased array transducer probe 110 of the girth weld 30.

If $Z < Z_0$, $E = [T^* \tan(\text{Angle Start})] + [Z^* \tan(\text{Start Incident Angle})] + P_X$ (26)

If $Z >= Z_0$, $E = [T^* \tan(\text{Angle Start})] + [Z^* \tan(\text{Start Incident Angle})] - P_X$ (27)

If $D < 0.5^* W_C$, $D = 0.5^* W_C$ (28)

In some cases, the positions for conducting the ultrasonic scan for the weld root 34 and the single access ultrasonic scan may be the same if the ultrasonic wedge 120 would be at the same position for both scans based on the location of the weld cap 32 as discussed above with respect to FIG. 3 and equations (25) and (28).

Returning to FIG. 6, if at step 610, if the inspection plan creation software determines that the ultrasonic scan for the weld cap 32 also covers the weld root 34 (e.g., if $\alpha <= \alpha_{TH}$), at step 612, the inspection plan creation software determines whether the ultrasonic wedge 120 and the phased array transducer probe 110 can be positioned on both sides (dual access) of the girth weld 30 or on only one side (single access). If there is access to perform an ultrasonic scan on both the left (first) side (i.e., on the first conduit 10) and the right (second) side (i.e., on the second conduit 20) of the girth weld 30 (FIG. 2), the inspection plan creation software determines that only one ultrasonic scan (or pass) of the weld cap 32 on each side of the girth weld 30 (performed in steps 614 (first side) and 616 (second side)) is required for complete coverage of the girth weld 30, the first heat-affected area 14, and the second heat-affected area 24. If there is only access to perform an ultrasonic scan on one side of the girth weld 30, the inspection plan creation software determines that a total of two ultrasonic scans (or passes) may be needed on that side of the girth weld 30 (e.g., for scanning the weld cap 32 on that side (in step 618) and for a single access scan (in step 620)).

Figure 7:
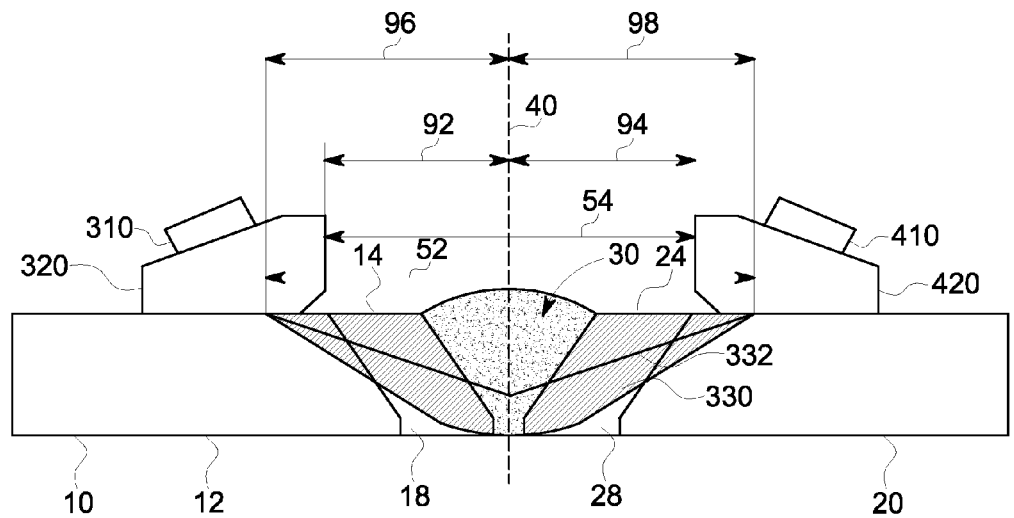
FIG. 7 illustrates an exemplary pair of TOFD probes and ultrasonic wedges positioned to conduct an ultrasonic scan of an exemplary girth weld between two conduits.

FIG. 7 illustrates an exemplary pair of TOFD probes 310, 410 and ultrasonic wedges 320, 420 positioned to conduct an ultrasonic scan of an exemplary girth weld 30 between two conduits 10, 20. Similar to the process described above in FIG. 6 for the phased array transducer probe 110, the inspection plan creation software can also automatically determine the horizontal probe center separation distance (PCS) 52 and the horizontal wedge front to front distance (DFF) 54 between the ultrasonic wedges 320, 420 by determining the inspection procedure, the selected wedge and probe parameters, and the weld and conduit parameters. In doing so, the inspection plan creation software can also automatically determine the distances 96, 98 between the centerline 40 and the probe centers of the ultrasonic wedges 320, 420, and automatically determine the distances 92, 94 between the centerline 40 and the wedge fronts of the ultrasonic wedges 320, 420.

As shown in FIG. 7, the ultrasonic center beam 332 emitted by the first TOFD probe 310 produces an ultrasonic beam spread 330 that provides coverage of the girth weld 30 except for the bottom portion 18 of the first heat-affected area 14 and the bottom portion 28 of the second heat-affected area 24. The inspection plan creation software can automatically determine the number of ultrasonic scans required for coverage of the girth weld 30 by determining whether the ultrasonic scan conducted at the automatically determined position of the ultrasonic wedges 320, 420 and the probes on 310, 410 the conduits 10, 20 will cover the weld cap 32 and the weld root 34 of the girth weld 30. To provide the additional coverage required to cover these bottom portions 18, 28 of the heat-affected areas 14, 24, the inspection plan creation software can automatically determine the offset required to reposition the TOFD probes 310, 410 and ultrasonic wedges 320, 420.

Figure 8:
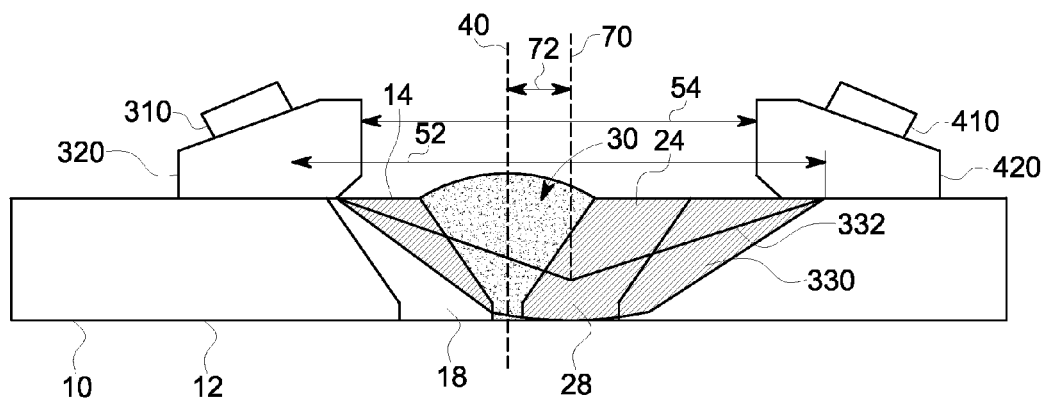
FIG. 8 illustrates an exemplary pair of TOFD probes and ultrasonic wedges positioned to conduct an ultrasonic scan of an exemplary girth weld between two conduits, offset from the position of FIG. 7.

FIG. 8 illustrates an exemplary pair of TOFD probes 310, 410 and ultrasonic wedges 320, 420 positioned to conduct an ultrasonic scan of an exemplary girth weld 30 between two conduits 10, 20, offset from the position of FIG. 7. The inspection plan creation software can determine the offset centerline 70 and the offset distance 72 required to have the ultrasonic beam spread 330 provide complete coverage of the girth weld 30, including the bottom portion 28 of the second heat-affected area 24.

Figure 9:
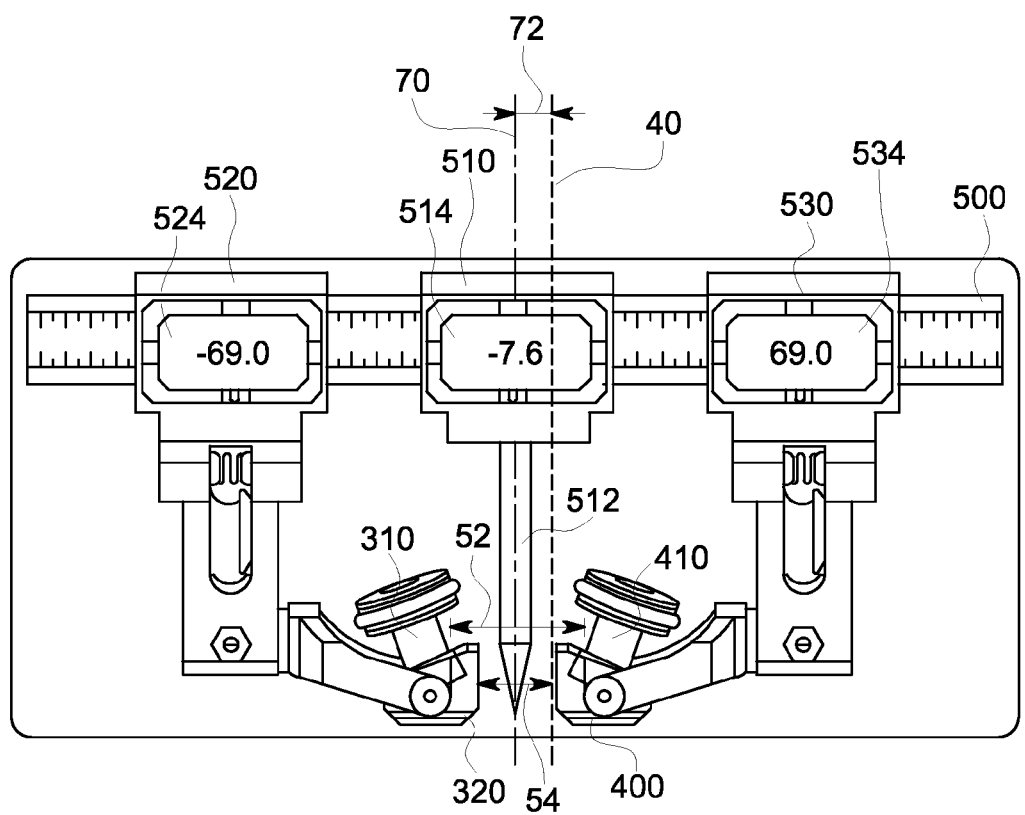
FIG. 9 illustrates an exemplary image of a scanner ruler for positioning a pair of TOFD probes and ultrasonic wedges to conduct an ultrasonic scan.

FIG. 9 illustrates an exemplary image of a scanner ruler 500 for positioning the pair of TOFD probes 310, 410 and ultrasonic wedges 320, 420 to conduct an ultrasonic scan using an offset as in FIG. 8. This image can be shown to an inspection technician on the display 170 of the ultrasonic inspection station 160 (FIG. 1) to provide instructions on positioning the TOFD probes 310, 410 and ultrasonic wedges 320, 420. The information about the scanner ruler 500 and its related dimensions is part of the inspection plan prepared by the inspection plan creator, which provides the proper position of the devices for conducting the ultrasonic scan. As shown in FIG. 9, the inspection plan calls for the center scanner ruler attachment 510 to be positioned on the offset centerline 70 at the center scanner ruler attachment position 514 (e.g., −7.6 mm) on the scanner ruler 500. A weld centerline locator 512 extends from the center scanner ruler attachment 510 to facilitate placement of the center scanner ruler attachment 510 on the weld centerline 40 prior to adjustment for the offset. The inspection plan calls for the left scanner ruler attachment 520 to be positioned at a certain left scanner ruler attachment position 524 (e.g., −69.0 mm) and the right scanner ruler attachment 530 to be positioned at a certain left scanner ruler attachment position 534 (e.g., 69.0 mm).

In view of the foregoing, embodiments of the method are disclosed for automatically positioning the ultrasonic wedge and the probe based on a number of parameters, including parameters that are based on the particular ultrasonic wedge and the probe as well as parameters based on the dimensions of the conduit and the girth weld. An advantage that may be realized in the practice of some disclosed embodiments of the positioning method is to simplify the procedure of determining the correct position and the number of ultrasonic scans required.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "service," "circuit," "circuitry," "module," and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A system for conducting an ultrasonic scan of a girth weld between a first conduit and a second conduit:
   an ultrasonic wedge mounted on a first conduit;
   a probe mounted to a probe interface wall of the ultrasonic wedge;
   an ultrasonic inspection station connected to the probe by a probe cable, wherein the ultrasonic inspection station comprises a display; and
   a computer for creating an inspection plan, wherein the computer comprises a display, a microprocessor, a memory coupled to the microprocessor, and one or more executable instructions stored in the memory and configured to be executed by the processor for creating the inspection plan, the executable instructions including instructions for:
      determining an inspection procedure to be used for the ultrasonic scan;
      determining a first plurality of parameters for the ultrasonic wedge and the probe;
      determining a second plurality of parameters for the girth weld and at least one of the first conduit or the second conduit; and
      determining a position of the ultrasonic wedge and the probe on at least one of the first conduit or the second conduit for the ultrasonic scan based on the inspection procedure to be used, the first plurality of parameters, and the second plurality of parameters.

2. The system of claim 1, wherein the probe is a phased array transducer probe.

3. The system of claim 1, wherein the probe is a time of flight diffraction (TOFD) transducer probe.

4. The system of claim 1, further comprising executable instructions for displaying on the display of the ultrasonic inspection station an image of the automatically determined position of the ultrasonic wedge and the probe on a scanner ruler.

5. The system of claim 1, further comprising executable instructions for automatically determining the number of ultrasonic scans required for coverage of the girth weld by determining whether the ultrasonic scan conducted at the automatically determined position of the ultrasonic wedge and the probe on at least one of the first conduit or the second conduit will cover the weld cap and the weld root of the girth weld.

* * * * *